(12) United States Patent
Hart et al.

(10) Patent No.: US 8,156,945 B2
(45) Date of Patent: Apr. 17, 2012

(54) SKIN CARE DEVICE

(76) Inventors: Karmen C. Hart, Benton, AR (US); Carolyn L. Jones, Little Rock, AR (US)

(\*) Notice: Subject to any disclaimer, the term of this patent is extended or adjusted under 35 U.S.C. 154(b) by 183 days.

(21) Appl. No.: 12/634,676

(22) Filed: Dec. 9, 2009

(65) Prior Publication Data

US 2011/0132385 A1 Jun. 9, 2011

(51) Int. Cl.
*A45D 29/18* (2006.01)
(52) U.S. Cl. ........................... 132/76.4
(58) Field of Classification Search .......... 132/73, 132/75.6, 76.4, 320
See application file for complete search history.

(56) References Cited

U.S. PATENT DOCUMENTS

| | | | |
|---|---|---|---|
| 1,604,685 A * | 10/1926 | Everitt | 132/75.6 |
| 5,082,009 A | 1/1992 | Cromer | |
| 5,913,313 A | 6/1999 | Brunderman | |
| 6,210,350 B1 | 4/2001 | Finch | |
| 6,226,811 B1 | 5/2001 | Fagan | |
| 6,253,407 B1 | 7/2001 | Bjelkevig | |
| D476,446 S | 6/2003 | Chen | |
| 6,708,351 B2 | 3/2004 | Sullinger | |
| 7,278,431 B2 | 10/2007 | Anderson et al. | |

\* cited by examiner

*Primary Examiner* — Rachel Steitz
(74) *Attorney, Agent, or Firm* — Michael G. Smith, Esq.

(57) ABSTRACT

Systems, methods and apparatus are provided through which in some implementations an abrasive exterior is attached to a body about obtuse to a right-angle of a trapezoid geometry of the body. In some implementations, the body includes a pocket along a longitudinal axis of the body and in some implementations the body includes a groove along a lateral axis.

20 Claims, 10 Drawing Sheets

FIG. 10

SKIN CARE DEVICE

FIELD

This disclosure relates generally to personal hygiene products, and more particularly to epidural removal apparatus.

BACKGROUND

Removing calluses and other undesirable epidural matter is performed using a number of apparatus, such as an emery board or a file. For example, U.S. Pat. No. 5,913,313 discloses an abrasive means attached to an end of a round handle. In another example, U.S. Pat. No. 7,278,431 discloses an abrasive means attached to a base floor apparatus. In yet another example, U.S. Pat. No. D476,446 discloses an abrasive means attached to a singular handle. In still another example, U.S. Pat. No. 5,082,009 discloses an abrasive means attached to a dual-prong handle. In still yet another example, U.S. Pat. No. 6,253,407 discloses an abrasive means that is attached to an undulating floor base unit. In a further example, U.S. Pat. No. 6,708,351 discloses an abrasive surface attached to a concave base apparatus. In yet a further example, U.S. Pat. No. 6,210,350 discloses an abrasive surface attached to a convex base apparatus.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, an overview is described. In the second section, apparatus of implementations are described. In the third section, implementations of methods are described. Finally, in the fourth section, a conclusion of the detailed description is provided.

In one aspect, an apparatus to remove calluses from skin includes a body having a pocket or recess along a longitudinal axis and a groove along a lateral axis, the body having a trapezoid geometry along the longitudinal axis and a right-angled trapezoid geometry along a vertical axis, and the apparatus also having an abrasive exterior surface attached to the body opposite to the right-angle of the trapezoid geometry.

In another aspect, an apparatus to remove calluses from skin includes a first side having a trapezoid geometry, a second side adjacent to the first side and having a right-angle trapezoid geometry, a third side adjacent to the first side and having the right-angle trapezoid geometry, a fourth side adjacent to the second side and the third side; wherein the fourth side having an abrasive exterior surface, and a fifth side adjacent to the first side, the second side, the third side and the fourth side; wherein the first side, the second side, the third side, the fourth side and the fifth side form a pocket.

In yet another aspect, an apparatus to remove calluses from skin includes a first outer surface forming a trapezoid, the first outer surface having four perimeters, two of the four perimeters being parallel to each other and the other two of the four perimeters being not parallel to each other, a second outer surface forming a first convex right-angle trapezoid, the second outer surface being adjacent to one of the two of the four perimeters being not parallel to each other, a third outer surface forming a second convex right-angle trapezoid, the third outer surface being adjacent to the other one of the two of the four perimeters being not parallel to each other; wherein the first convex right-angle trapezoid of the second outer surface is complementary to the second convex right-angle trapezoid of the third outer surface, a fourth outer surface having a third convex surface that is adjacent to the second outer surface and adjacent to the third outer surface, the fourth outer surface having an abrasive exterior surface; wherein the length of the fourth outer surface is less than the length of the first outer surface, and a fifth outer surface have a fourth convex surface, the fifth outer surface being adjacent to the second outer surface, adjacent to the third outer surface and adjacent to the fourth outer surface; wherein the first outer surface, the second outer surface, the third outer surface, the fourth outer surface and the fifth outer surface form a pocket.

In still another aspect, an apparatus to remove calluses from skin includes a first outer surface forming a trapezoid, the first outer surface having four perimeters, two of the four perimeters being parallel to each other and the other two of the four perimeters being not parallel to each other, a second outer surface forming a first convex right-angle trapezoid, the second outer surface being adjacent to one of the two of the four perimeters being not parallel to each other and the second outer surface having a first abrasive exterior surface, a third outer surface forming a second convex right-angle trapezoid, the third outer surface being adjacent to the other one of the two of the four perimeters being not parallel to each other, and the third outer surface having a second abrasive exterior surface; wherein the first convex right-angle trapezoid of the second outer surface is complementary to the second convex right-angle trapezoid of the third outer surface, a fourth outer surface having a third convex surface that is adjacent to the second outer surface and adjacent to the third outer surface, the fourth outer surface having a third abrasive exterior surface; wherein the length of the fourth outer surface is less than the length of the first outer surface, a fifth outer surface have a fourth convex surface, the fifth outer surface being adjacent to the second outer surface, adjacent to the third outer surface and adjacent to the fourth outer surface; wherein the first outer surface, the second outer surface, the third outer surface, the fourth outer surface and the fifth outer surface form a pocket; wherein the pocket has a first inner surface forming a trapezoid, the first inner surface having four perimeters, two of the four perimeters being parallel to each other and the other two of the four perimeters being not parallel to each other, a second inner surface forming a first right-angle trapezoid, the second inner surface being adjacent to one of the two of the four perimeters being not parallel to each other, a third inner surface forming a second right-angle trapezoid, the third inner surface being adjacent to the other one of the two of the four perimeters being not parallel to each other, and the third inner surface having a second abrasive exterior surface; wherein the first right-angle trapezoid of the second inner surface is complementary to the second right-angle trapezoid of the third inner surface, a fourth inner surface having a third convex surface that is adjacent to the second inner surface and adjacent to the third inner surface, the fourth inner surface having a third abrasive exterior surface, and a fifth inner surface have a fourth convex surface, the fifth inner surface being adjacent to the second inner surface, adjacent to the third inner surface and adjacent to the fourth inner surface.

Apparatus, systems, and methods of varying scope are described herein. In addition to the aspects and advantages described in this summary, further aspects and advantages will become apparent by reference to the drawings and by reading the detailed description that follows.

Overview

The overview of an implementation is described in this section of the detailed description.

Figure 1:
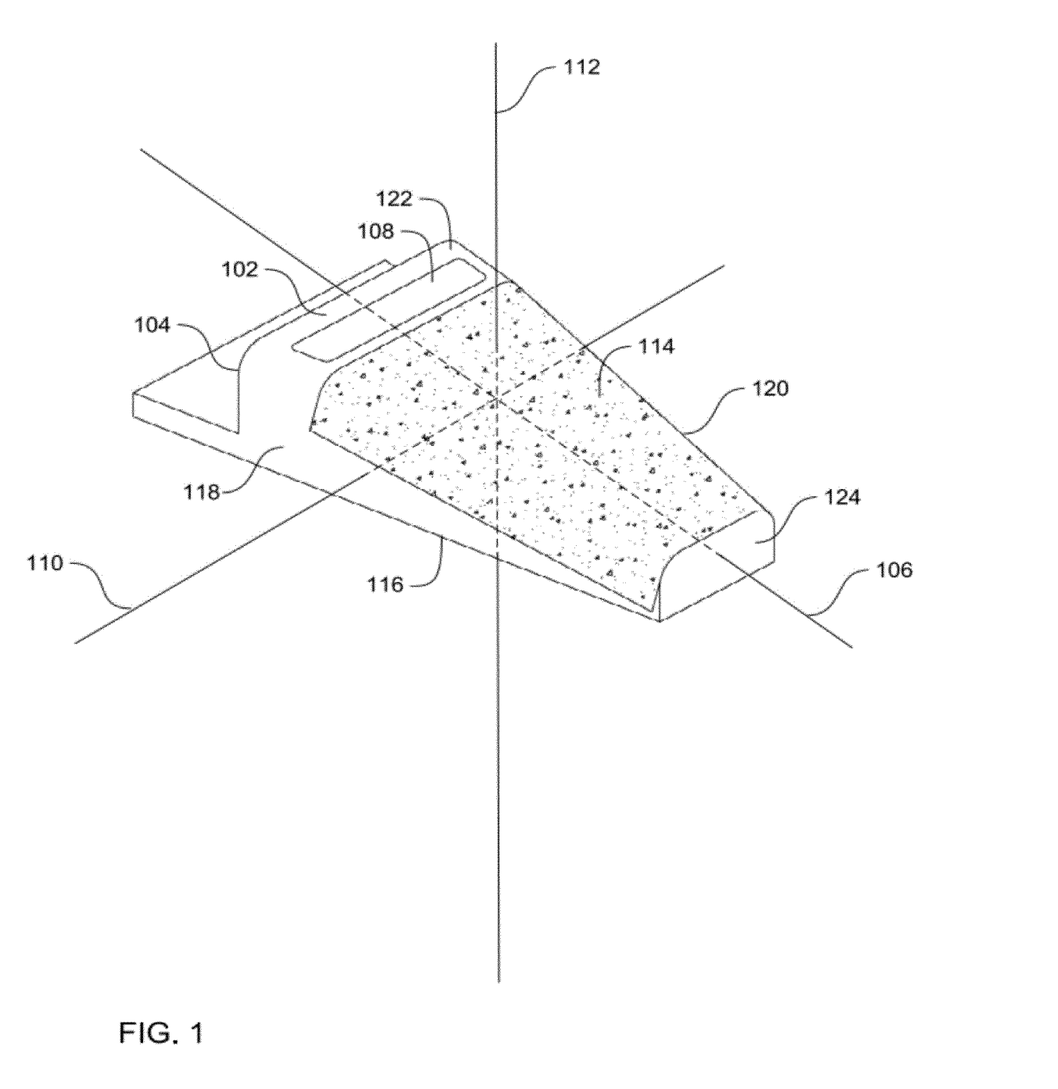
FIG. 1 is an isometric diagram of an overview of an apparatus to remove calluses from feet, according to an implementation.

FIG. 1 is an isometric diagram of an overview of an apparatus 100 to remove calluses from feet, according to an implementation.

Apparatus 100 includes a body 102. The body forms a pocket 104 along a longitudinal axis 106. Some implementations of body 102 have an isosceles trapezoidal geometry along the longitudinal axis 106. Other implementations of body 102 have a non-isosceles trapezoidal geometry along the longitudinal axis 106 that is in general proportion as the medial and the lateral sides of an average size adult human foot.

Some implementations of body 102 include a groove 108 along a lateral axis 110. The body 102 has a right-angled trapezoid geometry along a vertical axis 112. In some examples, the body 102 includes a polycarbonate resin thermoplastic known as Lexan®, and in other implementations, the body 102 consists of only a polycarbonate resin thermoplastic. In other examples, the body 102 includes a plastic, wood, or other hard formable material. Examples of plastic other than the ploycabonate resin thermoplastic include thermoset plastic, elastomer plastic, and thermoplastic. Thermoset plastic is hard and has a very tight-meshed, branched molecular structure. Curing of thermoset plastic proceeds during shaping, after which it is no longer possible to shape the thermoset plastic by heating. Further shaping of thermoset plastic may then only be performed by machining. Elastomer plastic has a crosslinked structure, with a looser mesh than thermosets, giving rise to a degree of elasticity. Once shaped, elastomer plastic cannot be reshaped by heating. Thermoplastic has a linear or branched molecular structure.

Apparatus 102 includes an abrasive exterior surface 114 that is attached to the body 102 opposite of the right-angle of the trapezoid geometry. The abrasive exterior surface 114 is implemented in any one of a number of variations, such as a wet-dry sandpaper, a sandpaper having grade 1 abrasiveness, a sandpaper having grade 2 abrasiveness, a sandpaper having 220 grit, a sandpaper having 320 grit, or a sandpaper having 400 grit. The wet-dry sandpaper can be cleaned while attached to the body.

In some implementations, the abrasive exterior surface 114 is fixedly attached or mounted to the body 102. In other implementations, the abrasive exterior surface 114 is removeably attached or mounted to the body 102. The removable abrasive exterior surface 114 can be replaced with new abrasive exterior surface 114 when the previous installation of the abrasive exterior surface 114 is worn out by losing the abrasive characteristics of the abrasive exterior surface 114 through use. In some implementations of the removable abrasive exterior surface 114, adhesive on the back of the removable abrasive exterior surface 114 provides adhesion of the removable abrasive exterior surface 114 to the body 102. The adhesive has a tackiness that is reasonable calculated to adhere the removable abrasive exterior surface 114 to the body 102 during typical use described below, yet is still sufficiently lacking in tackiness to permit removal of the removable abrasive exterior surface 114 by lifting a corner of the removable abrasive exterior surface 114 and peeling the remainder of the removable abrasive exterior surface 114 from the body 102.

The body 102 includes a first side 116 having the isosceles trapezoidal geometry. The first side 116 is also known as the "bottom". The body 102 also includes a second side 118 that is adjacent to the first side 116. The second side 118 has the right-angle trapezoid geometry. The second side 118 is also known as the "right side". The body 102 also includes a third side 120 that is adjacent to the first side 102. The third side 120 has the same right-angle trapezoid geometry as the second side 118. The third side 120 is also known as the "left side". The body 102 also includes a fourth side 122 that is adjacent to the second side 118 and adjacent to the third side 120. The fourth side 122 includes the abrasive exterior surface 114. The fourth side 122 is also known as "top". The body 102 also includes a fifth side 124 that is adjacent to the first side 116, adjacent to the second side 118, adjacent to the third side 120 and adjacent to the fourth side 122. The fifth side 124 is also known as the "toe" or "front".

In some implementations, some, any or all of the sides 116, 118, 120, 122 and/or 124 have a convex geometry that improves the angle at which the apparatus 100 is applied to a soft or keratinous surface. In one example, side 118, 120 and 122 have a rounded contour between sides 118 and 122 and between sides 120 and 122 that allow the apparatus 100 to be applied to a soft surface via a number of angles, thus providing more though abrasion and friction to the soft surface.

The first side 116, the second side 118, the third side 120, the fourth side 122 and the fifth side 124 form the pocket 114. The pocket 104 provides a place in which a foot or other appendage can be inserted to provide movement and leverage to the apparatus 100. When the apparatus 100 is positioned so that the abrasive exterior surface 114 is in contact with a callus or other soft surface, movement of the foot along the longitudinal axis 106 provides friction to the callus thru the abrasive exterior surface 114, thus shaving or reducing the callus.

While the apparatus 100 is not limited to any particular body 102, pocket 104, longitudinal axis 106, groove 108, lateral axis 110, vertical axis 112, abrasive exterior surface 114, first side 116, second side 118, third side 120, fourth side 122 and fifth side 124, for sake of clarity, a simplified body 102, pocket 104, longitudinal axis 106, groove 108, lateral axis 110, vertical axis 112, abrasive exterior surface 114, first side 116, second side 118, third side 120, fourth side 122 and fifth side 124 are described.

Apparatus Implementations

In the previous section, an overview of the operation of an implementation was described. In this section, particular implementations of apparatus are described by reference to a series of diagrams.

Figure 2:
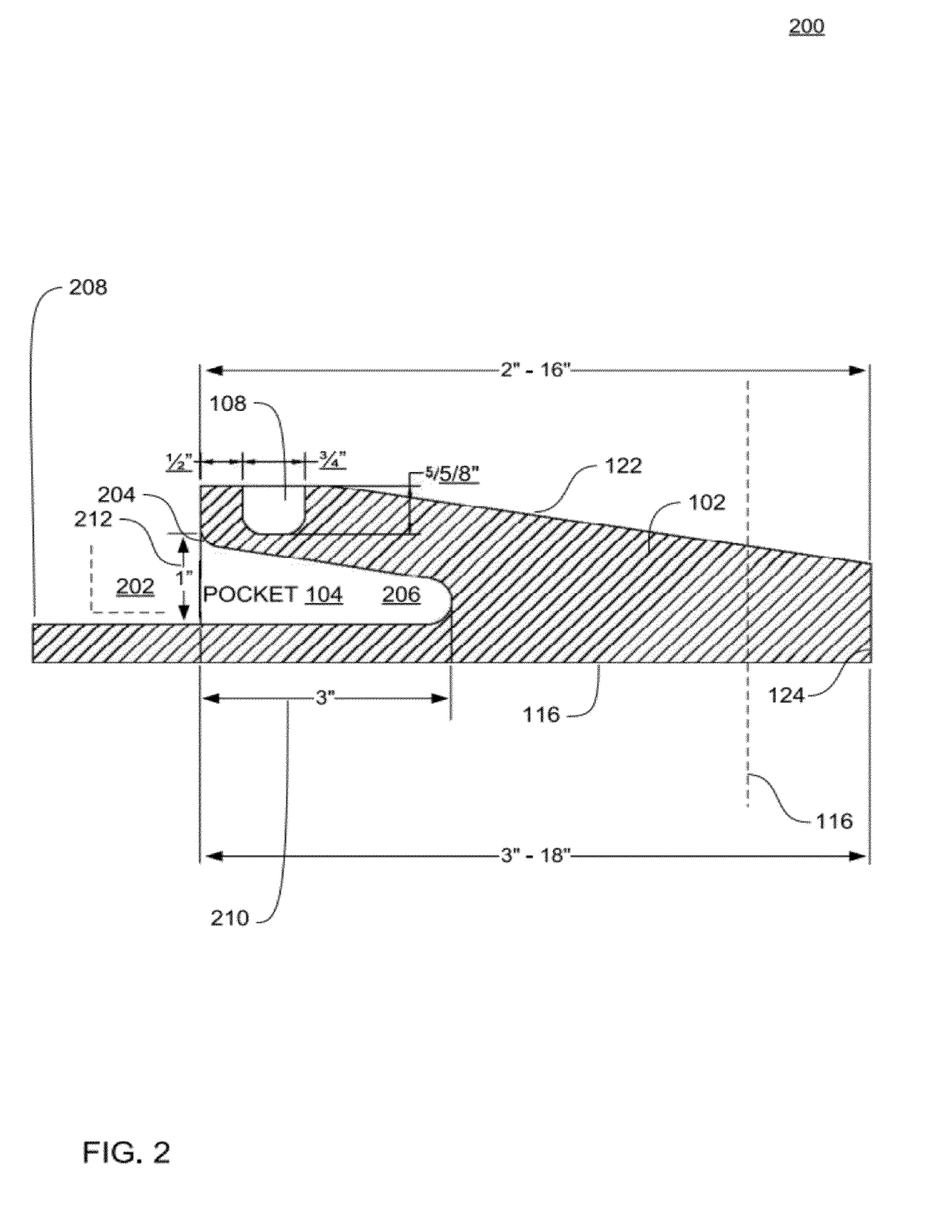
FIG. 2 is a cross-section block diagram of apparatus, according to an implementation having a groove.

FIG. 2 is a cross-section block diagram of apparatus 200, according to an implementation having a groove. The cross-section block diagram of apparatus 200 shows the body 102 sectioned vertically along the longitudinal axis 106 shown in FIG. 1.

Apparatus 200 includes a first side 116 that is also known as the "bottom". Apparatus 200 includes a fourth side 122 that is also known as "top". Apparatus 200 includes a fifth side 124 that is also known as the "toe" or "front".

Apparatus 200 includes a pocket 104 along the longitudinal axis 106. In the implementation shown in FIG. 2, the pocket has a depth of 3". In the implementation shown in FIG. 2, the pocket 104 has one, and only one, side that is open. The open side (the opening) of the pocket 104 is operable to receive a human foot or hand. The pocket 104 provides a place in which a foot or other appendage can be inserted to provide movement and leverage to the apparatus 200. When the apparatus 100 is positioned so that the abrasive exterior surface (114 in FIG. 1) is in contact with a callus or other soft surface, movement of the callus or other soft surface along the longitudinal axis 106 provides friction to the soft surface thru the abrasive exterior surface 114, thus shaving or reducing the surface. In some implementations, the pocket 104 has rounded contours for the comfort of the foot. For example, the pocket 104 has rounded contour edges at the top 204 of the opening and at the inside end 206 of the pocket 104.

Apparatus 200 includes a groove 108 along a lateral axis 110. In the implementation shown in FIG. 2, the groove 108 is positioned ½" from an edge of the top 122. In various implementations, the groove 108 is positioned from the edge of the top 122 in a range of ½" to 2". In the implementation shown in FIG. 2, the groove 108 has a depth of ⅝" and a width of ¾". In various implementations, the groove has a depth that ranges from ½" to 2" and a length that ranges between 2" to 6". When the apparatus 200 is positioned so that the toe 124 is positioned higher than the opposite side (unlabeled) of the apparatus 200, during operation in which movement of the callus or other soft surface along the longitudinal axis 106 provides friction to the soft surface thru the abrasive exterior surface 114, when the some of the shavings from the soft surface (e.g. callus) will fall down via operation of gravity into the groove 108, thus providing a cleaner working environment of the apparatus 200.

The body 102 has a right-angled trapezoid geometry 202 along a vertical axis 112.

In some implementations, the edge 208 is a rather sharp right-angle as shown in FIGS. 1, 2, 4-7 and 9. In some implementations not shown, the edge 208 is beveled or rounded. The depth 210 of the pocket 104 is shown in FIG. 2 as 3", however in various implementations, the depth 210 of the pocket ranges from 2" to 10". The opening height 212 of the pocket 104 is shown in FIG. 2 as 1", however in various implementations, the opening height 212 of the pocket 210 varies from 1" to 5".

Figure 3:
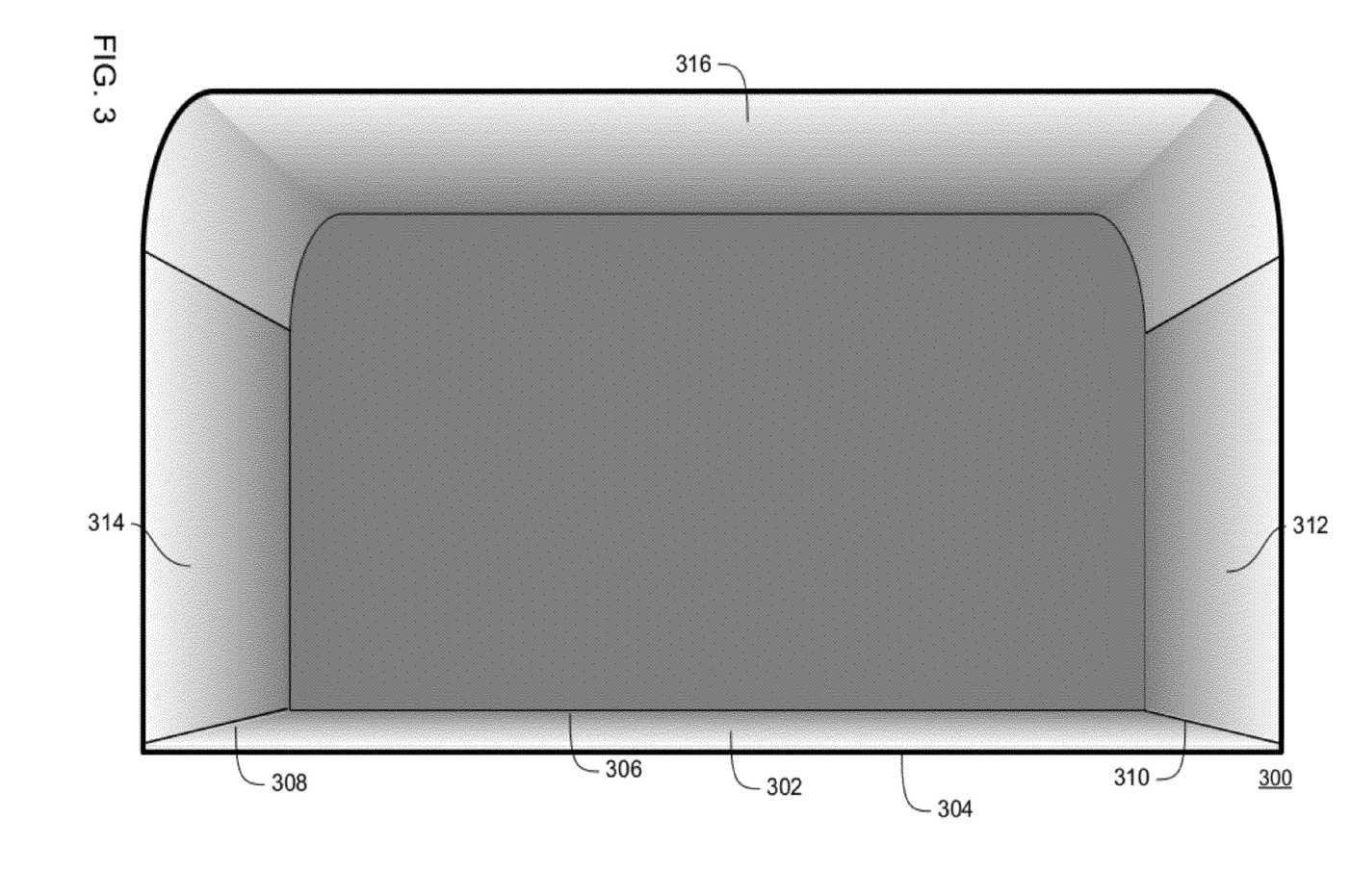
FIG. 3 is an isometric diagram of a pocket, according to an implementation.

FIG. 3 is an isometric diagram of a pocket 300, according to an implementation. Pocket 300 is one implementation of pocket 104 in FIG. 1.

Pocket 300 includes a first inner surface 302 forming a trapezoid. The floor 302 is also known as the floor of the pocket 300. The floor 302 has four perimeters 304, 306, 308 and 310. Two (304 and 306) of the four perimeters are parallel to each other and the other two (308 and 310) of the four perimeters are not parallel to each other;

Pocket 300 includes a second inner surface 312 that forms a first right-angle trapezoid. The second inner surface 312 is also known as the right wall. The right wall 312 is adjacent to perimeter 310, which is one of the two of the four perimeters that are not parallel to each other.

Pocket 300 includes a third inner surface 314 that forms a second right-angle trapezoid. The third inner surface 314 is also known as the left wall. The left wall 314 is adjacent to perimeter 308, which is the other one of the two of the four perimeters being not parallel to each other. In some implementations, the first right-angle trapezoid of the right wall 312 is complementary and symmetrical to the second right-angle trapezoid of the left wall 314.

Pocket 300 includes a fourth inner surface 316. The fourth inner surface 316 is also known as the roof. The roof 316 is adjacent to the right wall 312 and adjacent to the left wall 314.

Pocket 300 includes a fifth inner surface 318. The fifth inner surface 318 is also known as the end. The end 318 is adjacent to the right wall 312, adjacent to the left wall 314 and adjacent to the roof 316. In some implementations, the end 318 as a convex surface.

In some implementations, some, any or all of the inner surfaces 302, 312, 314 and/or 316 have a convex geometry. The convex geometry provides a more comfortable fit with a human foot.

Figure 4:
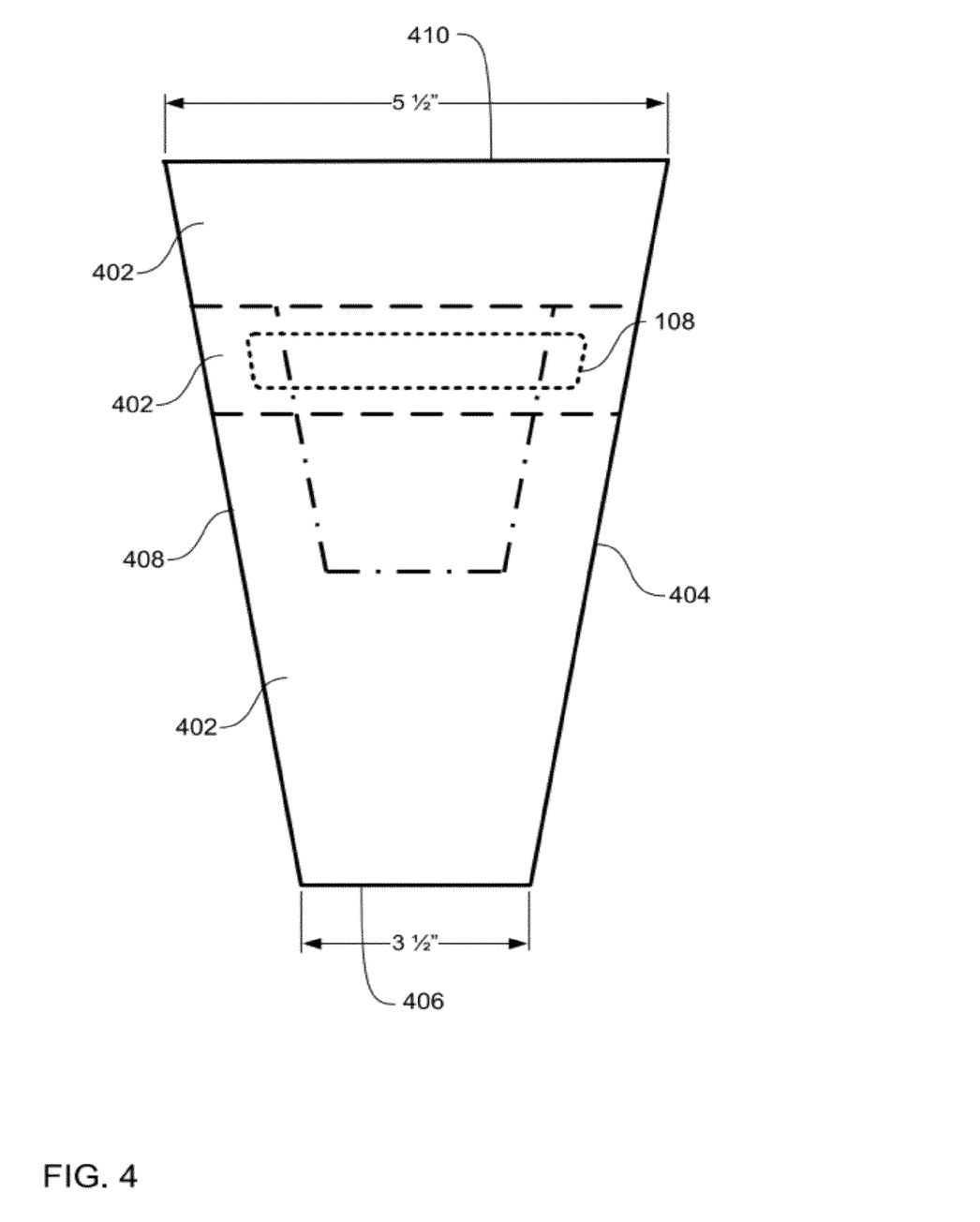
FIG. 4 is a bottom view block diagram of apparatus, according to an implementation of the bottom of the apparatus in FIG. 1.

FIG. 4 is a bottom view block diagram of apparatus 400, according to an implementation of the bottom 116 of apparatus 100.

Apparatus 400 has a first side 116 that includes a first outer surface 402 forming a trapezoid geometry. The first outer surface 402 has four perimeters; 404, 406, 408 and 410. Two of the four perimeters (304 and 408) are parallel to each other and the other two (306 and 410) of the four perimeters are not parallel to each other. In the implementation shown in FIG. 4, the perimeter 410 is shown as having a length of 5½", however in various implementations, the perimeter 410 has a length that ranges from 2" to 10".

In some implementations, the perimeters of the first outer surface 402 form an isosceles trapezoid geometry, such as shown in FIG. 4. In some implementations, the perimeters of the first outer surface 402 form a trapezoid geometry that is non-isosceles (not shown) whose geometry approximates the geometry of a typical foot.

In some implementations, the first outer surface 402 includes a rubber material that provides grip.

Figure 5:
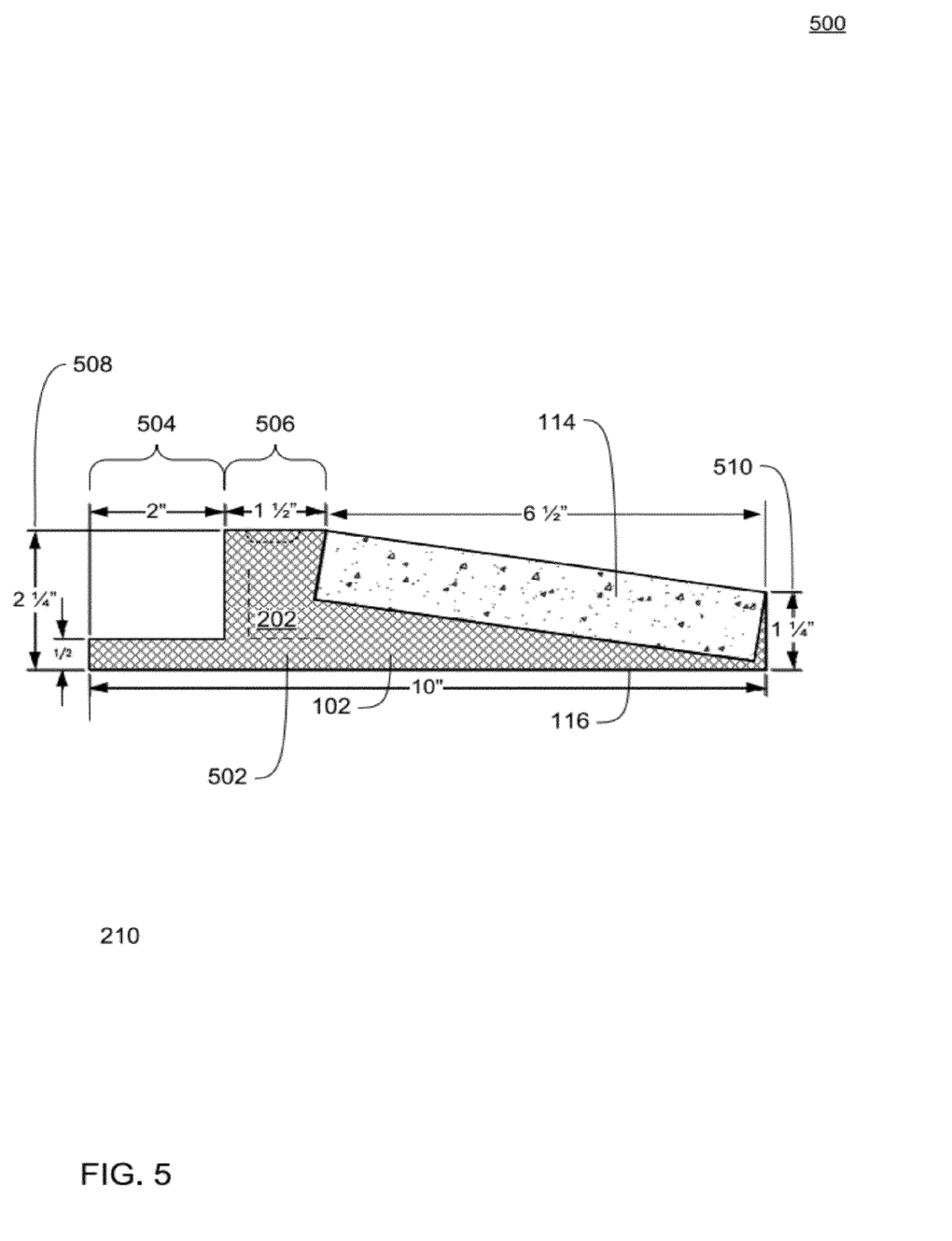
FIG. 5 is a right-hand side view block diagram of apparatus, according to an implementation of the right side of the apparatus in FIG. 1.

FIG. 5 is a right-hand side view block diagram of apparatus 500, according to an implementation of the right side 118 of apparatus 100.

Apparatus 500 has a second outer surface 502 that forms a first right-angle trapezoid geometry. Apparatus 500 includes an abrasive exterior surface 114 that is attached to the body 102, the abrasive exterior surface 114 is positioned or located opposite of the right-angle 202 of the trapezoid geometry of apparatus 500.

The second outer surface 502 is adjacent to one of the two perimeters (306 or 410 in FIG. 4) of the bottom 116 that are not parallel to each other.

In the implementation shown in FIG. 5, a notch 504 in the outer surface 502 is 2" in width and 1¾" inches in height above a ½" thick bottom side 116. The width of the notch 504 ranges in various implementations from ½" to 8". The implementation shown in FIG. 5 also includes a 1½" wide step 506 at the top of the outer surface 502. In various implementations, the bottom side 116 ranges in thickness from ½" to 10". In the implementation shown in FIG. 5, the height 508 of apparatus 500 is 2¼" however, in various implementations, the height ranges from 2" to 8". In the implementation shown in FIG. 5, the toe height 510 of apparatus 500 is 1¼" however, in various implementations, the toe height 510 ranges from 1" to 6".

The implementation shown in FIG. 5 also includes an abrasive outer surface that is approximately 6.5" in longitudinal length and approximately 6.6" in length.

Figure 6:
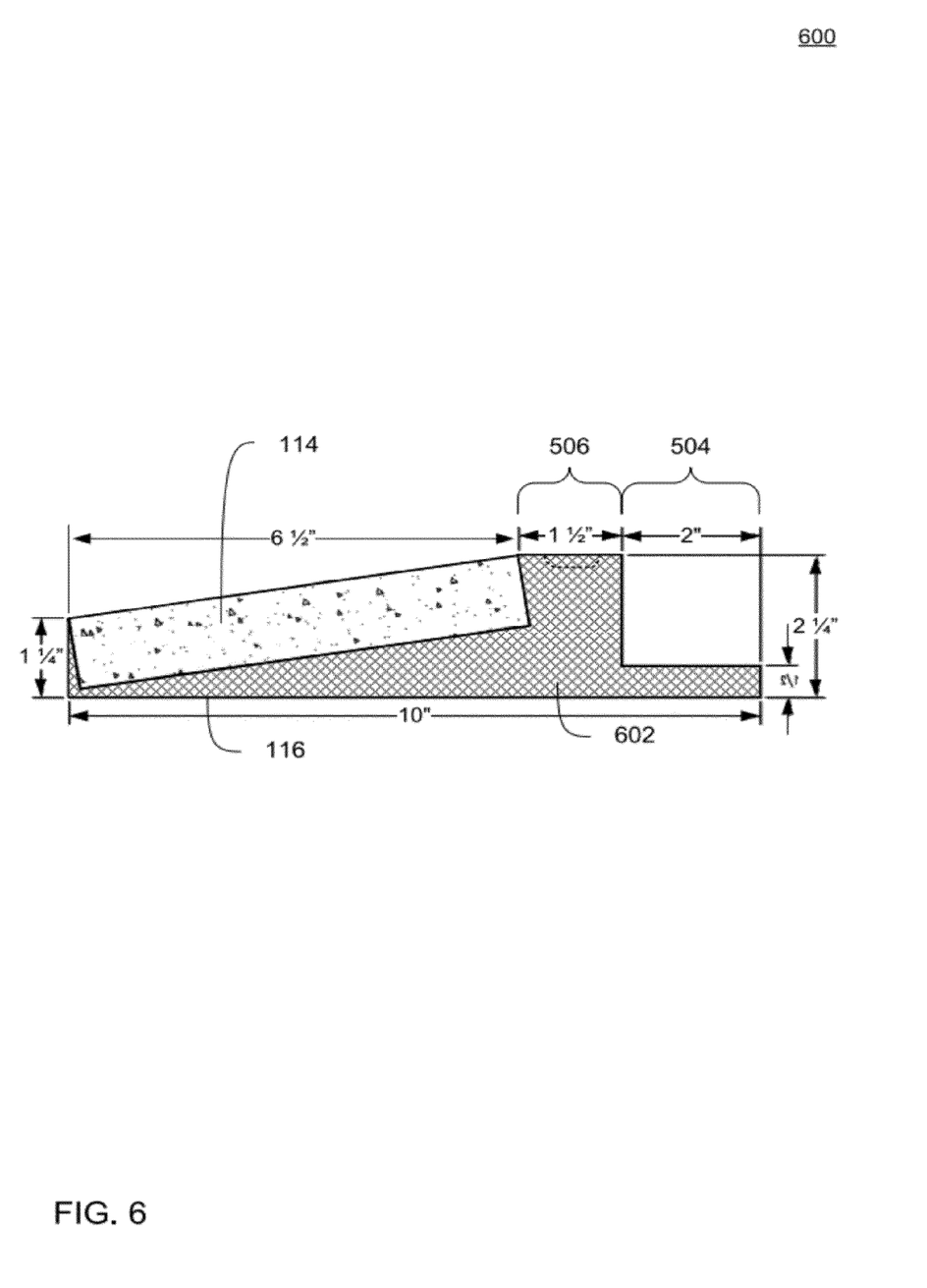
FIG. 6 is a left-hand side view block diagram of apparatus, according to an implementation of the left side of the apparatus in FIG. 1.

FIG. 6 is a left-hand side view block diagram of apparatus 600, according to an implementation of the left side 120 of apparatus 100.

Apparatus 600 has a third outer surface 602 that forms a second right-angle trapezoid geometry. The third outer surface 602 is adjacent to one of the two perimeters (306 or 410 in FIG. 4) of the bottom 116 that are not parallel to each other.

In the implementation shown in FIG. 6, the notch 404 in the outer surface 602 is 2" in width and 1¾" inches in height above a ½" high bottom side 116. The implementation shown in FIG. 6 also includes the step 406 that is 1½" wide and located at the top of the outer surface 602. The first right-angle trapezoid of the second outer surface 402 in FIG. 4 is complementary to the second right-angle trapezoid of the third outer surface 602 in FIG. 6.

The implementation shown in FIG. 6 also includes the abrasive outer surface 114 that is approximately 6.5" in longitudinal length and approximately 6.6" in length.

Figure 7:
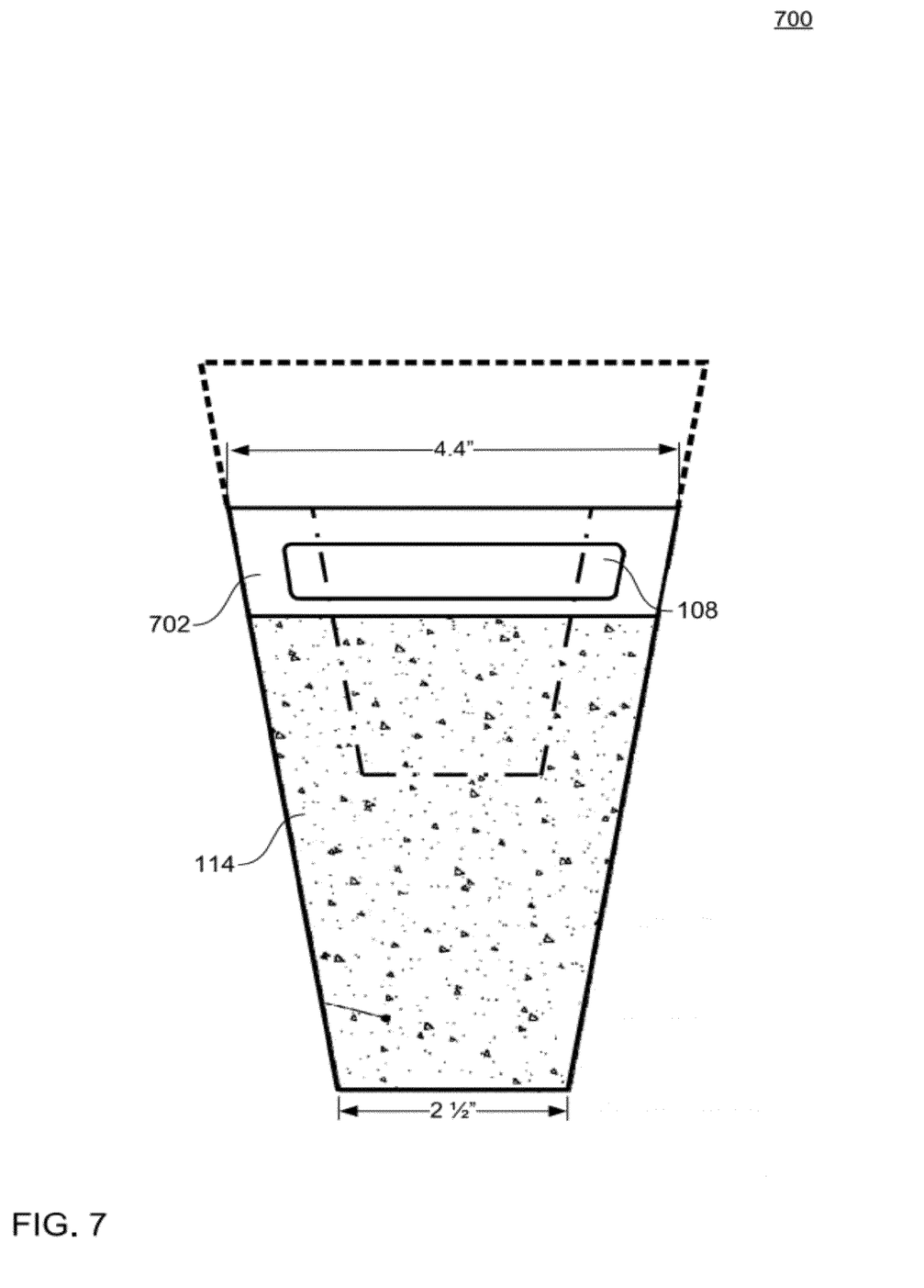
FIG. 7 is a top side view block diagram of apparatus, according to an implementation of the fourth side of the apparatus in FIG. 1.

FIG. 7 is a top side view block diagram of apparatus 700, according to an implementation of the fourth side 122 of apparatus 100. The fourth side 122 includes a fourth outer surface 702. The fourth side 122 is adjacent to the second side 118 and the fourth side is adjacent to the third side 120. The fourth side 122 includes the abrasive exterior surface 114. The length of the fourth outer surface 702 is less than the length of the first outer surface.

In some implementations, the abrasive exterior surface 114 includes the second outer surface 502 in FIG. 1, the third outer surface 602 in FIG. 6 and the fourth outer surface 702 in FIG. 7. In the implementation shown in FIG. 1, the fourth outer surface 702 of the fourth side 122 is geometrically blended with the second outer surface 502 of the right side 118 to form a continuous geometry between the fourth outer surface 702 of the fourth side 122 and the second outer surface 502 of the right side 118. Likewise, in the implementation shown in FIG. 1, the fourth outer surface 702 of the fourth side 122 is geometrically blended with the third outer surface 602 of the left side 120 to form a continuous geometry between the fourth outer surface 702 of the fourth side 122 and the third outer surface 602 of the right side 120.

Figure 8:
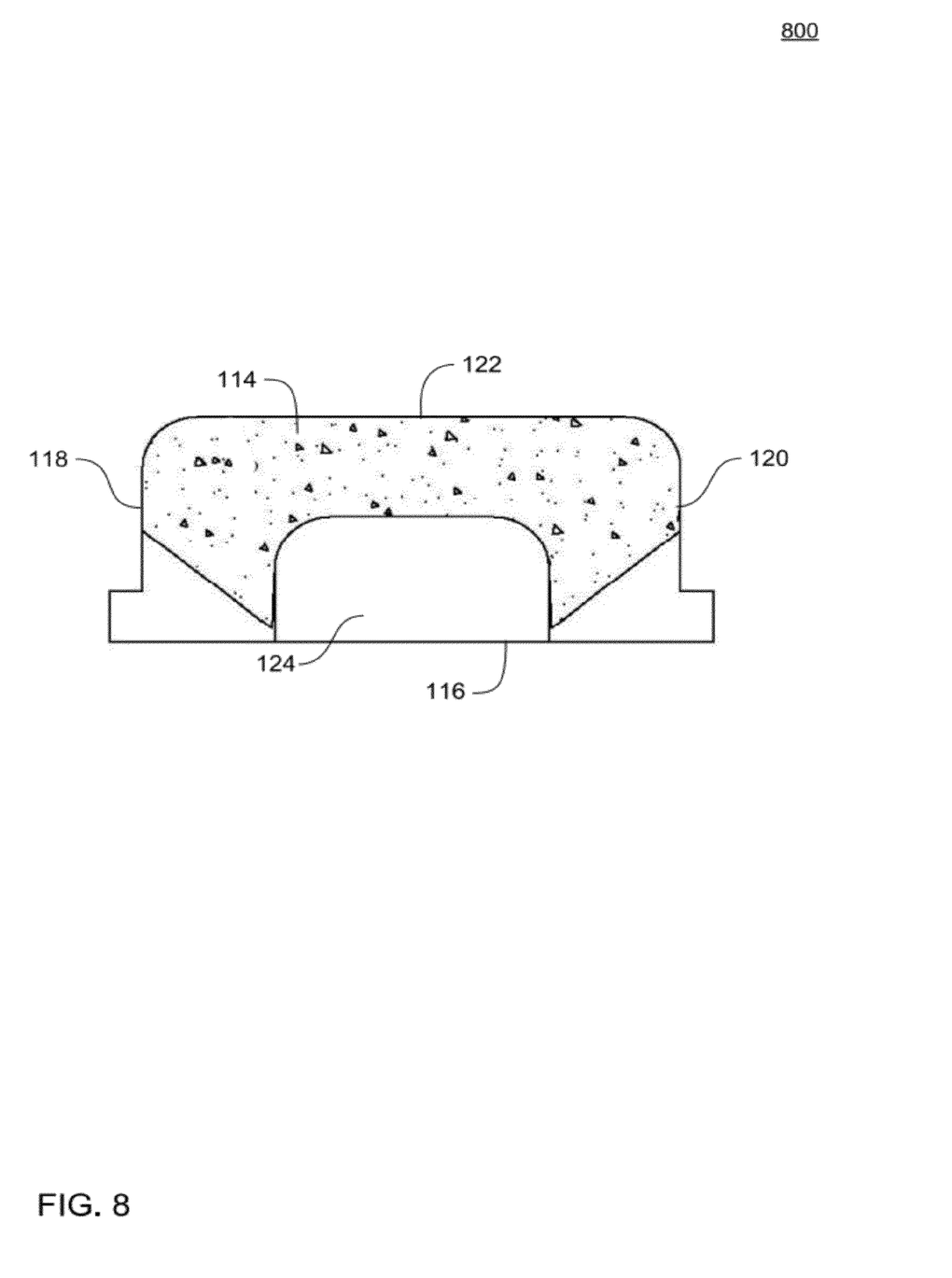
FIG. 8 is a front side view block diagram of apparatus, according to an implementation of the fifth side of the apparatus in FIG. 1.

FIG. 8 is a front side view block diagram of apparatus 800, according to an implementation of the fifth side 124 of apparatus 100. The fifth side 124 is adjacent to the first side 116, adjacent to the second side 118, adjacent to the third side 120 and adjacent to the fourth side 122.

Figure 9:
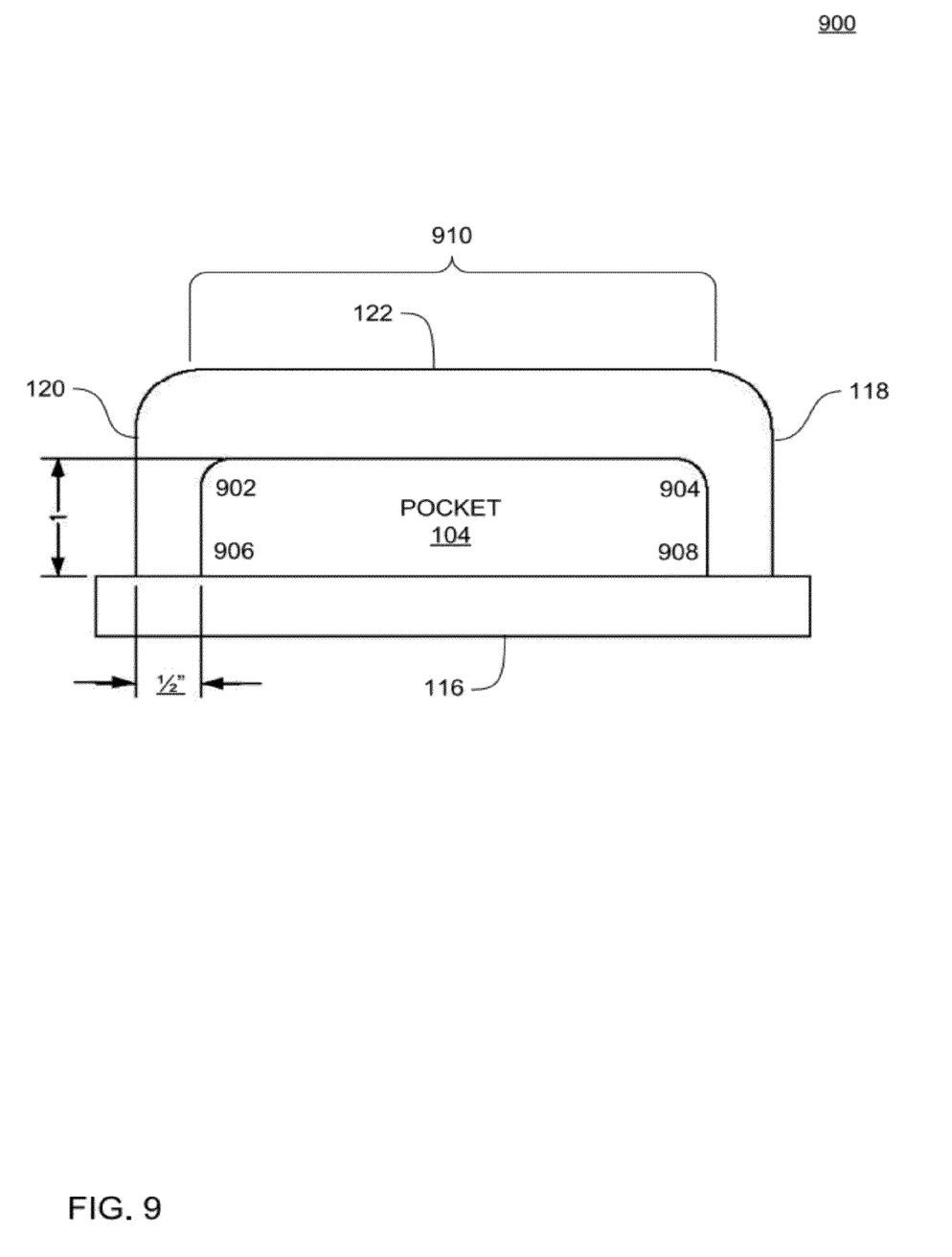
FIG. 9 is a back side view block diagram of apparatus, according to an implementation of the apparatus in FIG. 1.

FIG. 9 is a back side view block diagram of apparatus 900, according to an implementation of apparatus 100. Apparatus 100 includes the first side 116, the second side 118, the third side 120 and the fourth side 122. In apparatus 900, the thickness of the second side 118 and the third side 120 is about ½" and the height of the pocket 104 is about 1" at the opening of the pocket 104. In some implementations, such as shown in FIG. 2, the height of the pocket 108 decreases at locations further within the pocket 104. The decreasing height of pocket is in general proportion to the thickness of a typical adult human foot between the top of the foot adjacent to the bottom of the shinbone, to the end of the big toe.

In some implementations, the pocket 104 has rounded contours for the comfort of the foot. For example, the pocket 104 has rounded contour edges at the top left side 902 of the pocket and at the top right side 904 of the pocket 104. In some implementations not shown, the pocket 104 has rounded contour edges at the bottom left side 906 of the pocket and at the bottom right side 908 of the pocket 104.

In some implementations, the edge 910 is a rather sharp right-angle as shown in FIGS. 1, 2, 4-7 and 9. In some implementations not shown, the edge 910 is beveled or rounded.

The dimensions and relative proportions cited herein are merely exemplary and illustrative of particular implementations.

Method Implementations

In the previous section, apparatus of the operation of an implementation was described. In this section, the particular methods of such an implementation are described by reference to a series of flowcharts.

Figure 10:
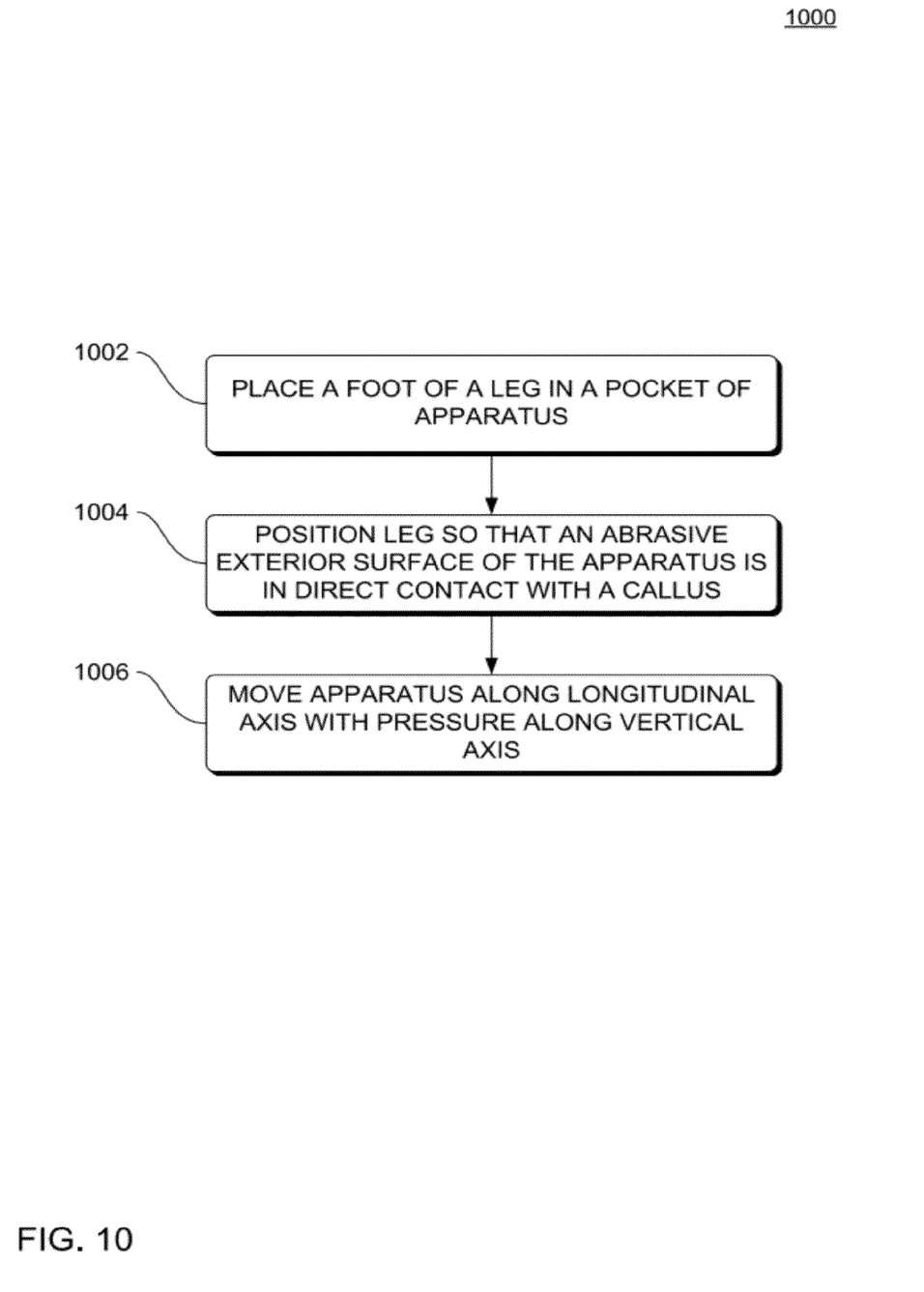
FIG. 10 is a flowchart of a method to shave or otherwise reduce the matter of a soft surface such as a foot callus, according to an implementation.

FIG. 10 is a flowchart of a method 1000 to shave or otherwise reduce the matter of a soft surface such as a foot callus, according to an implementation. Method 1000 provides a convenient and efficient technique of reducing callus matter from a foot without intervention by another human.

Method 1000 includes placing a foot of a leg in a pocket of an apparatus, such as apparatus 100, 200, 400, 500, 600, 700, 800 or 900. In response to placement of the foot in action 1002, method 1000 also includes positioning the leg in action 1004 so that an abrasive exterior surface (e.g. abrasive exterior surface 114) of the apparatus is in direct contact with a callus or other soft surface. In response to the positioning in action 1004, method 1000 also includes moving 1006 the apparatus along the longitudinal axis (e.g. 106) with pressure along the vertical axis (e.g. 112) in order the provide friction against the soft surface while keeping the abrasive exterior surface in contact with the soft surface, thus shaving or otherwise reducing the matter of the soft surface.

In various implementations, any of the edges or surfaces of apparatus and device described herein are beveled or rounded.

CONCLUSION

A skin care device is described. Although specific implementations are illustrated and described herein, it will be appreciated by those of ordinary skill in the art that any arrangement which is calculated to achieve the same purpose may be substituted for the specific implementations shown. This application is intended to cover any adaptations or variations. One of ordinary skill in the art will appreciate that implementations can be made other manners that provide the required function.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future abrasive devices, different body materials, and new dimensions and relative proportions.

The terminology used in this application is meant to include body materials, anatomic geometries and abrasive materials and alternate technologies which provide the same functionality as described herein

We claim:

1. An apparatus to remove calluses from skin, the apparatus comprising:
   a first outer surface forming a trapezoid, the first outer surface having four perimeters, two of the four perimeters being parallel to each other and the other two of the four perimeters being not parallel to each other;
   a second outer surface forming a first convex right-angle trapezoid, the second outer surface being adjacent to one of the two of the four perimeters being not parallel to each other and the second outer surface having a first abrasive exterior surface;
   a third outer surface forming a second convex right-angle trapezoid, the third outer surface being adjacent to the other one of the two of the four perimeters being not parallel to each other, and the third outer surface having a second abrasive exterior surface;
   wherein the first convex right-angle trapezoid of the second outer surface is complementary to the second convex right-angle trapezoid of the third outer surface;
   a fourth outer surface having a third convex surface that is adjacent to the second outer surface and adjacent to the third outer surface, the fourth outer surface having a third abrasive exterior surface, wherein the length of the fourth outer surface is less than the length of the first outer surface; and
   a fifth outer surface have a fourth convex surface, the fifth outer surface being adjacent to the second outer surface, adjacent to the third outer surface and adjacent to the fourth outer surface;
   wherein the first outer surface, the second outer surface, the third outer surface, the fourth outer surface and the fifth outer surface form a pocket,
   wherein the pocket has:
   a first inner surface forming a trapezoid, the first inner surface having four perimeters, two of the four perimeters being parallel to each other and the other two of the four perimeters being not parallel to each other;
   a second inner surface forming a first right-angle trapezoid, the second inner surface being adjacent to one of the two of the four perimeters being not parallel to each other;
   a third inner surface forming a second right-angle trapezoid, the third inner surface being adjacent to the other one of the two of the four perimeters being not parallel to each other, and the third inner surface having a second abrasive exterior surface;
   wherein the first right-angle trapezoid of the second inner surface is complementary to the second right-angle trapezoid of the third inner surface;
   a fourth inner surface having a third convex surface that is adjacent to the second inner surface and adjacent to the third inner surface, the fourth inner surface having a third abrasive exterior surface; and
   a fifth inner surface have a fourth convex surface, the fifth inner surface being adjacent to the second inner surface, adjacent to the third inner surface and adjacent to the fourth inner surface.

2. The apparatus of claim 1, wherein the first outer surface forming a trapezoid further comprises:
   the first outer surface forming an isosceles trapezoid.

3. The apparatus of claim 1, wherein each of the abrasive surfaces further comprises:
   a sandpaper having 320 grit.

4. The apparatus of claim 1, wherein each of the abrasive surfaces further comprises:
   a removable abrasive surface.

5. The apparatus of claim 4, wherein each of the removable abrasive surfaces further comprises:
   an adhesive.

6. The apparatus of claim 1 further comprising:
   a polycarbonate resin thermoplastic.

7. The apparatus of claim 1, wherein first outer surface further comprises:
   a rubber material.

8. An apparatus comprising:
   a first outer surface forming a trapezoid, the first outer surface having four perimeters, two of the four perimeters being parallel to each other and the other two of the four perimeters being not parallel to each other;
   a second outer surface forming a first convex right-angle trapezoid, the second outer surface being adjacent to one of the two of the four perimeters being not parallel to each other;
   a third outer surface forming a second convex right-angle trapezoid, the third outer surface being adjacent to the other one of the two of the four perimeters being not parallel to each other;
   wherein the first convex right-angle trapezoid of the second outer surface is complementary to the second convex right-angle trapezoid of the third outer surface;
   a fourth outer surface having a third convex surface that is adjacent to the second outer surface and adjacent to the third outer surface, the fourth outer surface having an abrasive exterior surface, wherein the length of the fourth outer surface is less than the length of the first outer surface; and
   a fifth outer surface have a fourth convex surface, the fifth outer surface being adjacent to the second outer surface, adjacent to the third outer surface and adjacent to the fourth outer surface;
   wherein the first outer surface, the second outer surface, the third outer surface, the fourth outer surface and the fifth outer surface form a pocket.

9. The apparatus of claim 8, wherein the abrasive exterior surface includes the second outer surface, the third outer surface and the fourth outer surface.

10. The apparatus of claim 8, wherein the first outer surface forming a trapezoid further comprises:
    the first outer surface forming an isosceles trapezoid.

11. The apparatus of claim 8, wherein each of the abrasive surfaces further comprises:
    a wet-dry sandpaper.

12. The apparatus of claim 8, wherein each of the abrasive surfaces further comprises:
    a sandpaper having grade of abrasiveness selected from the group of grades of abrasiveness consisting of grade 1 abrasiveness and grade 2 abrasiveness.

13. The apparatus of claim 8, wherein each of the abrasive surfaces further comprises:
    a sandpaper having a grit selected from the group of grits consisting of 220 grit, 320 grit and 400 grit.

14. The apparatus of claim 8, wherein each of the abrasive surfaces further comprises:
    a removable abrasive surface.

15. An apparatus comprising:
a first side having a trapezoid geometry, a second side adjacent to the first side and having a right-angle trapezoid geometry, a third side adjacent to the first side and having the right-angle trapezoid geometry, a fourth side adjacent to the second side and the third side, wherein the fourth side having an abrasive exterior surface, and a fifth side adjacent to the first side, the second side, the third side and the fourth side;
wherein the first side, the second side, the third side, the fourth side and the fifth side form a pocket;
wherein the first side further comprises:
a first outer surface forming the trapezoid geometry, the first outer surface having four perimeters, two of the four perimeters being parallel to each other and the other two of the four perimeters being not parallel to each other;
wherein the second side further comprises:
a second outer surface forming a first right-angle trapezoid, the second outer surface being adjacent to one of the two of the four perimeters being not parallel to each other;
wherein the third side further comprises:
a third outer surface forming a second convex right-angle trapezoid, the third outer surface being adjacent to the other one of the two of the four perimeters being not parallel to each other,
wherein the first convex right-angle trapezoid of the second outer surface is complementary to the second convex right-angle trapezoid of the third outer surface.

16. The apparatus of claim 15, wherein the abrasive exterior surface includes the second outer surface, the third outer surface and the fourth outer surface.

17. The apparatus of claim 15, wherein first outer surface further comprises:
a rubber material.

18. The apparatus of claim 15, wherein the abrasive exterior surface further comprises:
a removable abrasive surface.

19. The apparatus of claim 18, wherein the removable abrasive surface further comprises:
an adhesive.

20. The apparatus of claim 15 further comprising:
a polycarbonate resin thermoplastic.

\* \* \* \* \*